United States Patent [19]
Müller-Lierheim et al.

[11] Patent Number: 4,789,634
[45] Date of Patent: Dec. 6, 1988

[54] CARRIER FOR THE CULTIVATION OF HUMAN AND/OR ANIMAL CELLS IN A FERMENTER

[75] Inventors: Wolfgang G. K. Müller-Lierheim, Gräfelfing; Andreas H. Beiter, Munich, both of Fed. Rep. of Germany

[73] Assignee: Dr. Müller-Lierheim KG Biologische Laboratorien, Planegg, Fed. Rep. of Germany

[21] Appl. No.: 875,545

[22] Filed: Jun. 18, 1986

[30] Foreign Application Priority Data

Apr. 10, 1986 [EP] European Pat. Off. ............. 86104889
Jun. 18, 1985 [DE] Fed. Rep. of Germany ........ 3521684
Aug. 26, 1985 [DE] Fed. Rep. of Germany ........ 3530440

[51] Int. Cl.$^4$ ................................................ C12M 1/40
[52] U.S. Cl. ..................................... 435/288; 435/181; 435/285
[58] Field of Search ............... 435/284, 287, 288, 310, 435/285, 286, 180, 181, 177, 240, 241; 521/56

[56] References Cited

U.S. PATENT DOCUMENTS

| 4,048,018 | 9/1977 | Coughlin et al. | 435/288 |
| 4,209,591 | 6/1980 | Hendriks | 435/288 |
| 4,237,033 | 12/1980 | Scattergood | 435/284 |
| 4,568,706 | 2/1986 | Noetzel et al. | 521/56 |
| 4,612,288 | 9/1986 | Bigwood et al. | 435/181 |

FOREIGN PATENT DOCUMENTS

| 98084 | 9/1983 | Japan | 435/288 |
| 615841 | 2/1980 | Switzerland | 435/288 |
| 872547 | 10/1981 | U.S.S.R. | 435/181 |

*Primary Examiner*—Samuel Scott
*Assistant Examiner*—Noah Kamen
*Attorney, Agent, or Firm*—Fleit, Jacobson, Cohn & Price

[57] ABSTRACT

A carrier for the cultivation of animal and/or human cells in a fermenter, comprises a polymer base body of a solid formed into a pressure-resistant matrix, with a capillary system for carrying the liquid cell culture medium therethrough, with no cell growth occurring therein, and with interstices for three-dimensional cell growth therein, growth factors for the cells being covalently bonded to the boundary surfaces of the interstices. The carrier can provide a high level of cell density of the order of magnitude of $10^9$ cells/ml, by three-dimensional cell growth.

10 Claims, 1 Drawing Sheet

CARRIER FOR THE CULTIVATION OF HUMAN AND/OR ANIMAL CELLS IN A FERMENTER

BACKGROUND OF THE INVENTION

The present invention relates generally to a carrier for the cultivation of animal cells in a fermenter. In this specification any reference to animal cells is intended also to embrace human cells, so that the carrier is thus suitable for the cultivation of human cells and/or animal cells.

In order to provide for growth of adherent animal cells on the fixed surface of a substrate, the substrate must have a surface nature such as to permit the cells satisfactorily to adhere thereto. Surfaces with a positive or a negative electrical charge have been found to be suitable substrates for that purpose. Adhesion and growth factors are also known, for example bivalent cations, fibronectin or serum, which are applied to plastic surfaces in order to promote adhesion and growth of the cells thereon. The electrical charge on the surface of the substrate causes absorption of the adhesion and growth factors on which the cells thus grow. However certain types of cells can themselves synthesize fibronectin and of themselves are therefore capable of growing on charged plastic surfaces, for example diploid fibroblasts. Other cells however necessitate the addition of serum or fibronectin to the culture medium. As will be appreciated however, the addition of serum or fibronectin to the culture medium as adhesion or growth factors give rise to a considerable increase in the cost of cell cultivation ant it is undesirable in many cases, for example in the production of therapeutics.

Adherent animal, including human, cells, in particular connective tissue cells, form a cell growth which permits only a single layer of cells, being what is referred to as a monolayer. That means that the cells can only grow in two dimensions. It is thus necessary to use very substantial surface areas in order to achieve high levels of cell density, which are required in a technical use situation. That is achieved for example by using spherical carrier bodies, also referred to as microcarriers, consisting of cross-linked dextran, with denatured collagen being covalently bonded to the surface thereof. The glutinous dextran bodies are distributed by stirring in the culture medium. The soft consistency of the carrier bodies or microcarriers is intended to reduce damage to or erosion of the grown cells in the event of collisions between the carrier bodies during the stirring operation. If the growth-bearing carrier bodies come into contact with each other and adhere to each other, it is possible to provide for three-dimensional cell culture (reference may be made in this respect to the brochure entitled 'Microcarrier cell culture principles & methods' from Pharmacia Fine Chemicals AB, of Uppsala). However, that procedure does not make it possible to achieve controlled three-dimensional cell growth, which is a necessary condition if cell densities as occur in a human or animal body (about $10^9$ cells/ml) are to be achieved.

Also known is the hollow fiber module through which the cell culture medium is passed. Cell growth takes place in the interstices between the fibers. When that occurs, a gradient in respect of cell feed with the cell culture medium is formed in the longitudinal direction of the hollow fiber module.

Another known arrangement involes using porous ceramic cartridges through which the cell culture medium is passed. It is also known to provide for microencapsulation of the cells, with cells being encapsulated in Na-alginate and the alginate droplets being enclosed with a polymer network. The alginate is then dissolved out of the network. Those known processes also can only achieve cell densities of the order of magnitude of around $10^7$ cells/ml.

SUMMARY OF THE INVENTION

An object of the present invention is to provide a carrier for cultivation of animal cells, including therefrom human cells as indicated above, which provides a cell growth with cell densities of up to approximately the cell densities of $10^9$ cells/ml to be found in a human or animal body.

Another object of the invention is to provide a carrier for the cultivation of animal cells in a fermenter, to permit the cultivation of even sensitive cells in synthetic medium without serum additive.

Yet another object of the present invention is to provide a carrier for cultivating animal cells, such as to optimize cell reproduction.

A further object of the invention is to provide a carrier for animal cell cultivation in a fermenter, which provides a secure basis for cell growth.

Still a further object of the present invention is to provide an animal cell cultivation carrier which is such as to provide for reliable feed of cell culture medium to the cells and removal of cell metabolism products.

In accordance with the principles of the present invention, these and other objects are achieved by a carrier for the cultivation of animal cells, which as defined thus comprises human and/or animal cells, in a fermenter with a polymer base substance, growth factors for the cells being covalently bonded to the surface thereof. The base substance in the fermenter comprises a solid which is formed into a pressure-resistant matrix with a capillary system transmissive in respect of the liquid cell culture medium, in which no cell growth occurs. The matrix solid has spaces or interstices for three-dimensional cell growth, with the growth factors being bonded to the boundary surfaces thereof.

Thus, in the carrier in accordance with the present invention, the base body forms a solid bed in which cell growth occurs, the bed being inherently stable insofar as being resistant to pressure, more particularly a flow pressure. The bed has two different internal inherently stable interstices areas, in one of which the interstices may be formed by the contours of beads of a bead polymer and serve for three-dimensional cell growth. The other capillary interstices in the solid bed may be formed by macropores of the beads of the bead polymer, the macropores being of such small pore diameters that cells cannot grow thereinto, while however being such as to permit the liquid cell culture medium to flow therethrough, thereby ensuring that the cells are always supplied with the cell culture medium and cell metabolism products are removed. That thus gives a continuous cell growth. The carrier which is provided in accordance with the present invention may accordingly be a component of a tissue fermenter which is economical in operation and in which animal and/or human cell lines occur in large-scale or mass culture.

The fact that the carrier body is in the form of a fixed, unmoving matrix means that it is possible to provide an arrangement for three-dimensional growth of animal, including human, cells. The carrier bodies are coated with growth factors which are bonded to the interface between the fixed matrix with respect to the interstices into which three-dimensional cell growth takes place.

The matrix has a capillary system, formed for example by the macropores of a bead polymer, into which the cells cannot grow. However, as indicated above, the capillary system serves to provide a feed of cell culture medium for the cells and for removal of cell metabolism products. The matrix may be formed by bead-like base bodies which, as already indicated above, may be of a macroporous nature, with the pores forming the capillary system. The surfaces of the beads are coated with the growth factors and in the matrix form the boundary surfaces of the interstices in which three-dimensional cell growth occurs.

In an advantageous aspect the invention further provides that, when using the carrier according to the invention, it is possible to eliminate the addition of serum of fibronectin or other adhesion and growth factors, to the culture medium. In a preferred feature of the invention, the adhesion and growth factors which may be for example glycoproteins, in particular from serum and preferably in that case from fetal calf serum, as well as fibronectrin, are preferably covalently bonded to the surface of the polymer body by way of oxirane groups. A suitable bead material for the polymer body is for example the commercially available bead polymer described in 'forum mikrobiologie' 8 (1985) page 296.

For the purposes of bonding the adhesion or growth factors to the carrier body, in particular to the surfaces thereof which define the above-mentioned interstices in which three-dimensional cell growth occurs, it is possible to use other covalent bonding modes, as are disclosed for example in 'Angewandte Chemie 94' (1982), page 838 or 'Chemiker-Zeitung', 97th edition (1973) No 11, page 612 including use of an azide, a carbodiimide, an isothiocyanate, a cyanogen bromide, or an azo compound.

By charging the carrier bodies according to the invention which have the adhesion and growth factors at the surface thereof, with feeder cells, for example macrophages, it is possible to produce biologically active carrier materials, by means of which it is also possible to cultivate sensitive cells in a synthetic medium without serum additive. Cell reproduction but also secondary metabolism can be optimized by the use of suitable growth factors.

Further objects, features and advantages of the present invention will be apparent from the following description of a preferred embodiment, with reference to the accompanying drawing.

DESCRIPTION OF THE PREFERRED EMBODIMENT

Figure 1:
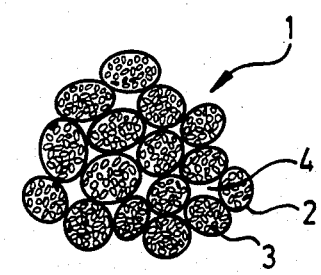
FIG. 1 is a diagrammatic view of part of an embodiment of a carrier which is formed from a bead polymer.

Referring firstly to FIG. 1, shown therein in diagrammatic form is a small portion of a matrix-like carrier 1 which is formed by a polymer 2, more particularly a bead polymer. Beads of the bead polymer, as indicated by reference numeral 2, are from about 50 to 300 $\mu$m, more particularly around 200 $\mu$m, in diameter. The beads 2 of the bead polymer have macropores as indicated at 3, the pore diameter thereof being smaller than around 10 $\mu$m, more particularly from 0.1 to 3.0 $\mu$m.

For example, as known in the art as disclosed in forum mikrobiologie 8 (1985), the beads are formed from bead polymers of methacrylamide, N-methylenebismethacrylamide, allylglycidylether or glycidylmethacrylate. The density is approximately 1.039 g/ml in water. The surfaces of the beads 2 are coated with growth factors such as peptides, proteins, hormones and the like, for animal cells. The surfaces of the beads 2 thus form boundary surfaces for gaps or interstices 4 in which threedimensional cell growth can occur. The macropores 3 of the beads form a capillary system into which the cells cannot grow as the cell diameter is about 20 $\mu$m. The capillary system is capable of passing the liquid growth medium therethrough, so that the cells can be supplied with the growth medium and cell metabolism products can be carried away therefrom, not only during the growth phase but also in the production phase (the stable phase). The metabolic effect is produced by a given flow pressure which is produced in the fermenter.

Figure 2:
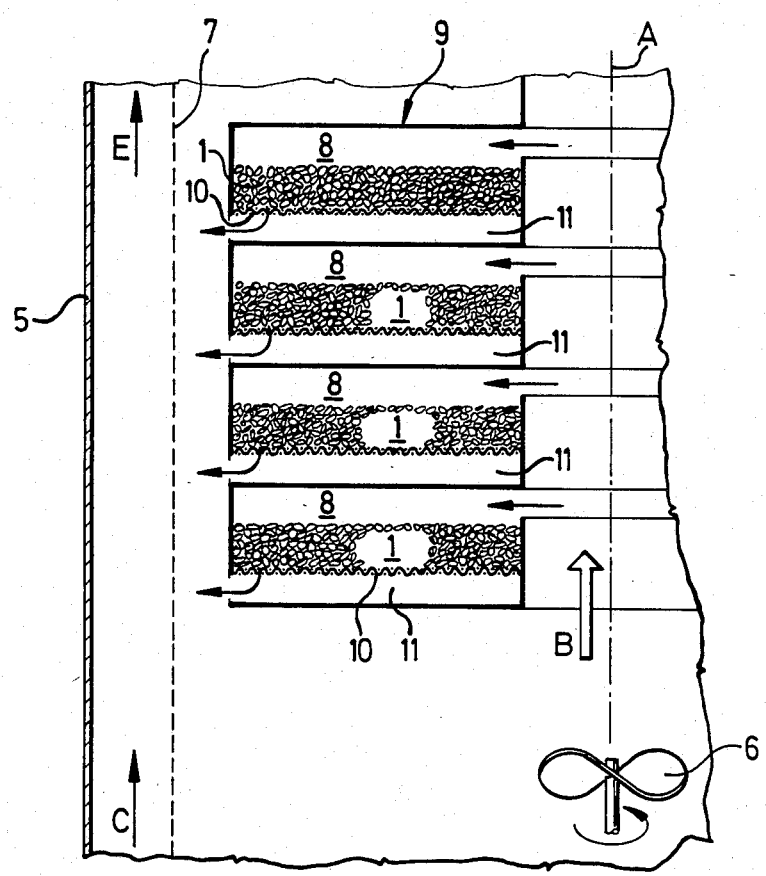
FIG. 2 is a diagrammatic view of a tissue fermenter using the carrier of bead polymer in the form of a fixed bed, in a particular arrangement.

Reference will now be made to FIG. 2 which is a diagrammatic view of part of a fermenter in which carriers 1 as arranged for example as shown in FIG. 1 are used in layer form, as a component of the fermenter. The thickness of the layers formed by the carriers 1 may be between 0.5 to 30 mm, depending on the cell type to be cultivated. The fermenter comprises a cylindrical casing 5 and a stirrer or agitator 6 which is disposed at a stationary location in the lower part of the fermenter, on the axial center line of the cylindrical casing 5, as indicated by A. The carriers 1 are arranged in superposed relationship and in annular layers around the center line A, in the interior of the fermenter. Disposed between the assembly of the carriers 1 and the fermenter casing 5 is a semipermeable foil 7. The stirrer 6 which may alternatively be replaced by a pump arrangement causes cell culture medium to be transported along the center line A in a flow in the direction indicated by arrow B, centrally and axially in the fermenter in the upward direction as shown in FIG. 2. The feed of cell culture medium into the fermenter may be in the direction indicated by the arrow C, between the fermenter casing 5 and the foil 7. It should be noted however that the direction of flow of the medium along the line A may also be in a downward direction.

The primary flow of the cell culture medium, which occurs centrally in the fermenter in the direction indicated by the arrow B branches radially outwardly into the intermediate spaces 8 defined between the layers of carriers 1. The cell culture medium which is to be found in the spaces 8 above the carriers 1 is under a flow pressure which is produced by the pump action of the stirrer 6, or of the alternative pump arrangement to which reference has been made above. By virtue of that flow pressure, the cell culture medium passes into the matrix of the carriers 1 which are arranged in superposed relationship in layers, and flows downwardly through the carrier layers.

The carriers 1 are arranged on sieve or screen members 10, in a frame indicated at 9 in FIG. 2. That arrangement ensures that, after the cell culture medium has passed through the layers of carriers 1, it can then flow downwardly into spaces 11 beneath the respective layers. While the cell culture medium is passing through the carriers 1, it gives off nutrients for cell growth. Even when the sizes of the interstices 4 are reduced by three-dimensional cell growth occurring therein, flow of the cell culture medium through the carriers and removal of cell metabolism products from the carriers 1 is always ensured because, as already referred to above in relation to FIG. 1, the matrix has a capillary system which is formed in the illustrated embodiment by the pores of the beads of the polymer, into which the cells cannot grow because of the respective dimensions thereof and which is sufficient to supply the cells with further fresh cell culture medium which is fed thereto from the spaces 8 above the layers of carriers 1, and to carry cell metabolism products into the spaces 11, after having passed through the carriers 1. The cell culture medium leaves the spaces 11 in a radially outward direction, as indicated by the flow arrows. Low molecular weight substances are exchanged through the semipermeable foil 7. The renewed medium is removed from the fermenter in an upward direction as indicated by arrow E. Proteins as products of secondary cell metabolism are retained and enriched.

The cell culture medium may conventionally include amino acids, carbon sources, in particular glucose and additives such as oxygen and carbon dioxide and possibly serum. The choice of culture medium depends on the nature of the cells to be cultivated.

Removal of the consumed nutrient medium in the direction indicated by the arrow E, upwardly from the fermenter, ensures that the level of lactate concentration in the fermenter is held at a low value, so that cell growth is not adversely affected.

It should also be appreciated that the feed of fresh cell culture medium may also occur within the semipermeable foil 7 which is cylindrical, like the casing 5.

It will be appreciated that the above-described carrier was set forth by way of example of the principles of the present invention and that various modifications may be made therein without thereby departing from the spirit and scope of the invention, and likewise in regard to the arrangement of the fermenter. Thus, in the described embodiment the bead polymer comprises beads which are of a diameter of from about 50 to 300 $\mu m$, but bead diameters of from 30 to 1000 $\mu m$ could also be employed. Also, as indicated, while the cell culture medium flows upwardly from the stirrer 6, into the spaces 8 and downwardly through the horizontally disposed layers of carriers 1, in the direction therefore of the thickness of the layers, it would also be possible to use a different flow configuration. Furthermore, any suitable growth factors may be employed, for example a combination of cell metabolism products and biochemically modified natural products.

We claim:

1. A carrier for the cultivation of animal cells in a fermenter, comprising a plurality of porous polymer beads, said beads having a diameter of from 50 to 300 $\mu m$ and said pores having a diameter from 0.1 to 3.0 $\mu m$, transmissive for liquid cell culture medium and in which no cell growth occurs, formed into a pressure-resistant matrix with interstices within which cell growth takes place, growth factors for the cells being attached to the boundaries defined by said interstices,
   wherein said beads are arranged on a sieve means in the fermenter, such that cell culture medium flows downwardly therethrough,
   wherein said fermenter is of a hollow cylindrical configuration and a plurality of said beads is arranged in a plurality of horizontal layers in superposed relationship in the fermenter, and wherein said fermenter comprises means for transporting the cell culture medium through the fermenter centrally along the axis of the cylindrical configuration thereof, then radially outwardly over said horizontal layers and then downwardly through said layers due to flow pressure of said medium.

2. A carrier as set forth in claim 1 wherein said growth factors are covalently bound.

3. A carrier as set forth in claim 1 wherein said beads are arranged in stationary relationship in the fermenter and in operation said cell culture medium flows therethrough.

4. A carrier as set forth in claim 3 wherein said beads are arranged in the form of one or more layers in the fermenter and in operation said cell culture medium flows therethrough in the direction of the thickness of said layers.

5. A carrier as set forth in claim 1 wherein the bonding of said growth factors is effected by oxirane groups.

6. A carrier as set forth in claim 1 wherein said growth factors are glycoproteins.

7. A carrier as set forth in claim 1 wherein said growth factors are selected from blood serum, blood serum constituents, fibronectin and fetal calf serum.

8. A carrier as set forth in claim 1 wherein said growth factors are a combination of cell metabolism products and biochemically modified natural products.

9. A carrier as set forth in claim 1 wherein spaces are provided on respective sides of said superposed layers, a said space above a respective layer serving to receive the radially outward flow of the cell culture medium and the other space beneath said respective layer serving to receive the flow of medium through said layer for discharge of said medium.

10. In a fermenter comprising an at least substantially cylindrical casing; means for introducing a flow of liquid cell culture medium into said casing; means for passing said flow of liquid cell culture medium substantially axially centrally through said fermenter; means for directing said flow as a plurality of branch flows in radially outward directions; perforate support means; means for passing said branch flows of cell culture medium downwardly through said perforate support means; and means for discharge of said cell culture medium from said casing; carriers on said support means, for the cultivation of animal cells, comprising a plurality of porous polymer beads, transmissive for liquid cell culture medium and within which no cell growth occurs, formed into a pressure-resistant matrix with interstices within which three-dimensional cell growth takes places, growth factors for the cells being bonded to the boundaries defined by said interstices.

* * * * *